(12) United States Patent
Corbucci

(10) Patent No.: US 8,391,975 B2
(45) Date of Patent: Mar. 5, 2013

(54) TELEMETRY OF COMBINED ENDOCAVITARY ATRIAL AND VENTRICULAR SIGNALS

(75) Inventor: Giorgio Corbucci, Cento (IT)

(73) Assignee: Medtronic, Inc., Minneapolis, MN (US)

(*) Notice: Subject to any disclaimer, the term of this patent is extended or adjusted under 35 U.S.C. 154(b) by 804 days.

(21) Appl. No.: 11/237,178

(22) Filed: Sep. 28, 2005

(65) Prior Publication Data

US 2007/0073347 A1    Mar. 29, 2007

(51) Int. Cl.
*A61N 1/365* (2006.01)

(52) U.S. Cl. .................. 607/17; 607/9; 607/11; 607/14

(58) Field of Classification Search ............. 607/9, 11, 607/14, 15, 17, 18, 27, 28, 122, 123
See application file for complete search history.

(56) References Cited

U.S. PATENT DOCUMENTS

| | | | | |
|---|---|---|---|---|
| 4,316,249 | A | * | 2/1982 | Gallant et al. ............... 600/515 |
| 4,407,289 | A | * | 10/1983 | Nappholz et al. ............ 607/14 |
| 4,791,936 | A | * | 12/1988 | Snell et al. ................... 607/27 |
| 5,117,824 | A | | 6/1992 | Keimel et al. |
| 5,193,550 | A | * | 3/1993 | Duffin .......................... 600/515 |
| 5,233,983 | A | * | 8/1993 | Markowitz .................. 607/42 |
| 5,275,621 | A | | 1/1994 | Mehra |
| 5,331,966 | A | * | 7/1994 | Bennett et al. ............... 607/28 |
| 5,354,319 | A | | 10/1994 | Wyborny et al. |
| 5,626,621 | A | * | 5/1997 | Skoglund et al. ............ 607/10 |
| 5,683,426 | A | | 11/1997 | Greenhut et al. |
| 6,250,309 | B1 | * | 6/2001 | Krichen et al. |
| 6,266,566 | B1 | * | 7/2001 | Nichols et al. ............... 607/30 |
| 6,418,346 | B1 | * | 7/2002 | Nelson et al. |
| 6,442,433 | B1 | * | 8/2002 | Linberg et al. |
| 6,456,881 | B1 | | 9/2002 | Bornzin et al. |
| 6,480,745 | B2 | * | 11/2002 | Nelson et al. |
| 6,482,154 | B1 | * | 11/2002 | Haubrich et al. |
| 6,574,511 | B2 | * | 6/2003 | Lee |
| 6,599,250 | B2 | * | 7/2003 | Webb et al. |
| 6,917,830 | B2 | * | 7/2005 | Palreddy et al. ............. 600/509 |
| 2002/0128688 | A1 | | 9/2002 | Stoop et al. |
| 2002/0143367 | A1 | * | 10/2002 | Levine et al. ................. 607/9 |
| 2002/0151812 | A1 | * | 10/2002 | Scheiner et al. ............. 600/528 |
| 2004/0127947 | A1 | | 7/2004 | Kim et al. |
| 2004/0193223 | A1 | * | 9/2004 | Kramer et al. ............... 607/9 |

(Continued)

FOREIGN PATENT DOCUMENTS

| | | |
|---|---|---|
| EP | 1529551 A | 5/2005 |
| WO | WO9320891 A | 10/1993 |

OTHER PUBLICATIONS

International Search Report, PCT/US2006/038210, Jan. 26, 2007, 8 Pages.

(Continued)

*Primary Examiner* — Joseph Dietrich
(74) *Attorney, Agent, or Firm* — Evans M. Mburu; Stephen W. Bauer

(57) ABSTRACT

A method for use in an implantable medical device system, comprising: selecting a first sensing electrode operatively disposed in a first heart chamber; setting a first sensing window corresponding to cardiac electrical events occurring in a second heart chamber; enabling a first sense amplifier coupled to the first sensing electrode during the first sensing window; sensing a first signal corresponding to cardiac electrical events occurring in the second heart chamber during the first sensing window using the first sensing electrode; and transmitting the first signal from an implantable medical device to an external monitor.

17 Claims, 9 Drawing Sheets

FIG. 1

U.S. PATENT DOCUMENTS

2004/0215089 A1 10/2004 Bergelson et al.

OTHER PUBLICATIONS

Office Action dated Dec. 27, 2007 for U.S. Appl. No. 11/237,080, 9 pages.
Response dated Mar. 18, 2008 for U.S. Appl. No. 11/237,080, 7 pages.
Office Action dated Jun. 18, 2008 for U.S. Appl. No. 11/237,080, 9 pages.
Response dated Aug. 13, 2008 for U.S. Appl. No. 11/237,080, 8 pages.
Advisory Action dated Sep. 2, 2008 for U.S. Appl. No. 11/237,080, 3 pages.
RCE dated Sep. 18, 2008 for U.S. Appl. No. 11/237,080, 1 page.
Office Action dated Oct. 6, 2008 for U.S. Appl. No. 11/237,080, 9 pages.
Response dated Feb. 6, 2009 for U.S. Appl. No. 11/237,080, 9 pages.

* cited by examiner

TELEMETRY OF COMBINED ENDOCAVITARY ATRIAL AND VENTRICULAR SIGNALS

BACKGROUND

1. Field of the Invention

The invention relates to medical devices, and, more particularly, to an implantable medical device system for providing ECG data without the use of external electrodes.

2. Description of the Related Art

Surface ECG tracings are routinely collected during a clinical follow-up visit of a patient having a cardiac pacemaker or implantable cardioverter defibrillator (ICD). The ECG tracings allow a clinician to observe electrical activities corresponding to the patient's heart rhythm, i.e. observe whether the rhythm is an intrinsic, normal sinus rhythm, or if the atrium and/or ventricles are being paced. The ECG tracings can also be analyzed for evidence of pacing capture, fusion, examined for changes due to ischemia, and used for measuring the duration of the P-wave and QRS-complex.

Acquisition of surface ECG tracings requires considerable preparation time. During an office visit, the patient is generally required to partially disrobe, and the surface ECG electrodes, typically 3 to 12, are placed on the skin at appropriate locations. The electrodes are then connected to an ECG monitor to first verify proper connection and then for observation or recording of the ECG traces. Sometimes patients are monitored through transtelephonic follow-ups. A surface ECG may be monitored transtelephonically by having the patient self-apply wrist or fingertip electrodes. Transtelephonic follow-ups are convenient for the patient since the patient does not need to travel to a clinic. Unfortunately, the quality of ECG signals so obtained is often poor.

Recently, remote patient monitoring systems have been introduced which allow data from an implantable medical device (IMD) such as a pacemaker or ICD to be uplinked telemetrically to a home monitor and transferred to a web-based patient management system accessible by an Internet-enabled computer. Such systems allow physicians to observe data retrieved from an IMD and manage the IMD performance and patient care independent of the patient's location. Remote patient management systems thereby reduce the time burden and inconvenience posed upon both the patient and the clinician normally associated with follow-up visits performed in a clinic. Long-range telemetry systems that enable the IMD to communicate with the home monitor without any patient intervention are proposed, making remote patient management even more convenient to the patient. However, if ECG tracings are desired during a remote follow-up session, the patient would be required to self-apply surface electrodes and such data would need to be transferred to the remote patient monitoring system.

ECG data made available without the use of surface ECG electrodes would clearly benefit the clinicians, nurses or other medical technicians and the patient by simplifying clinical follow-up visits and reducing the time required. Furthermore, ECG data made available without the use of surface ECG electrodes would allow remote patient follow-up sessions to be more complete without added burden to the patient.

DETAILED DESCRIPTION

In the following description, references are made to illustrative embodiments for carrying out the invention. It is understood that other embodiments may be utilized without departing from the scope of the invention. The invention is directed toward an IMD system and associated method for obtaining ECG data without the use of external, surface ECG electrodes. In the following description, references are made to "ECG" signals and to "EGM" signals. The term "ECG" signals, as used herein, refers to cardiac electrical signals obtained using far-field sensing electrodes. "Far-field sensing electrodes" refers to electrodes not located in or on the cardiac chamber in which the sensed cardiac electrical signals are originating.

Typically, ECG signals are obtained using surface ECG electrodes during a patient follow-up visit in a clinic. Various embodiments of the invention eliminate the need for applying surface ECG electrodes by utilizing far-field sensing electrodes included in the implanted IMD system for acquiring ECG signals. For example, and as will be described in detail herein, ventricular ECG signals may be acquired using implanted atrial sensing electrodes, and atrial ECG signals may be acquired using implanted ventricular sensing electrodes. The acquired ECG signals are made available for use by a clinician in evaluating a patient's heart rhythm and for evaluating IMD performance and operation.

The term "EGM signal(s)", as used herein, refers to cardiac electrical signals sensed using near-field electrodes. "Near field electrodes" refers to electrodes located in or on the same heart chamber in which the sensed cardiac electrical signals are originating. Generally, sensed EGM signals are used by the IMD in detecting heart rhythms, determining the need for a therapy, and controlling therapy delivery.

Figure 1:
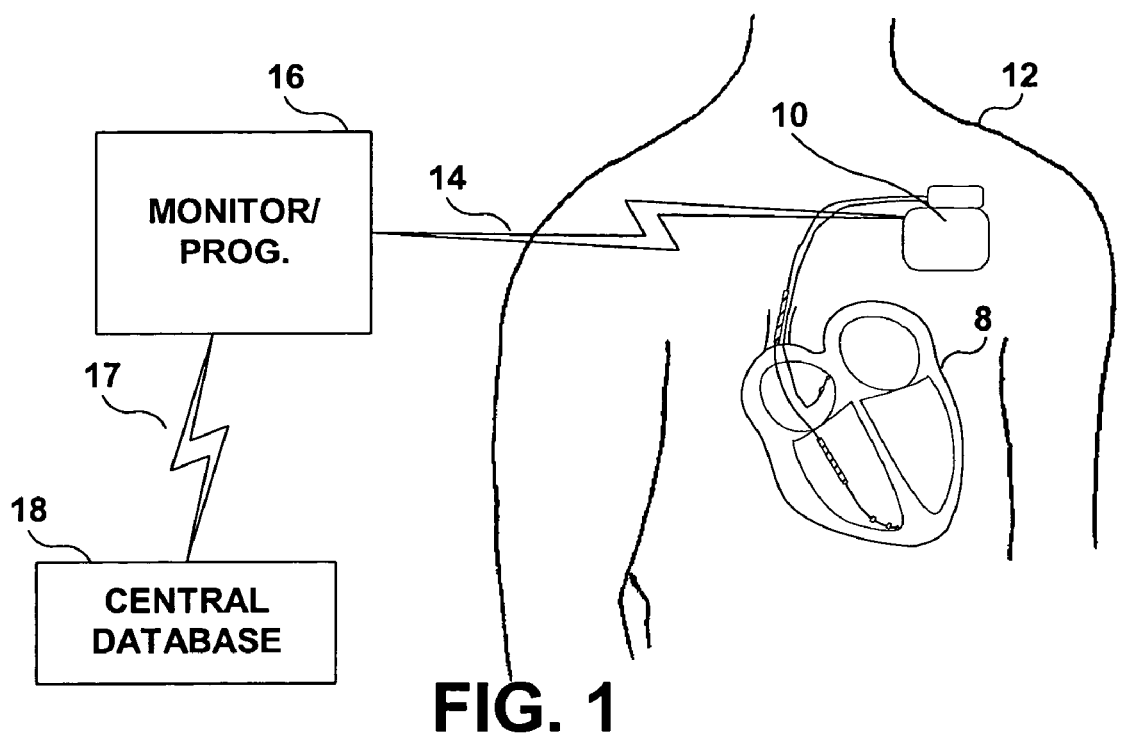
FIG. 1 illustrates an IMD system including an external monitor/programmer for communicating with an IMD.

FIG. 1 illustrates an IMD system including an external monitor for communicating with the IMD. IMD 10 is shown implanted in a patient 12 and is generally used for sensing cardiac electrical signals and for delivering electrical stimulation therapies in one or more heart chambers. In various embodiments, IMD 10 may include other monitoring and/or therapy delivery functions. The simplified illustration of IMD 10 shown in FIG. 1 may therefore represent a variety of IMDs such as cardiac pacemakers, implantable cardioverter defibrillators, hemodynamic monitors, ECG recorders, drug delivery devices, or neuromuscular stimulators. IMD 10 is coupled to one or more leads carrying electrodes disposed in operative relation to one or more chambers of heart 8 for monitoring cardiac electrical signals and delivering electrical stimulation therapies, as will be described below.

IMD 10 is provided with an antenna and associated circuitry for establishing a communication link 14 with external monitor/programmer 16.

External monitor/programmer 16 is provided for communicating with IMD 10 for retrieving real time or stored data from IMD 10. External monitor/programmer 16 may include programming functions for transferring programming commands to be implemented by IMD 10 for controlling IMD operations. External monitors and programmers for use with implantable medical devices are known in the art.

As will be described in greater detail herein, real-time or stored ECG data can be transferred to the external monitor/programmer 16 from IMD 10 through bi-directional communication link 14. External monitor/programmer 16 may optionally be adapted to communicate with a central database 18 to allow transfer of data retrieved from IMD 10 to the central database 18.

Central database 18, also referred to herein as "remote patient management database," may be an Internet-based or other networked database used for remote patient monitoring. External monitor/programmer 16 may be enabled to transfer data via communication link 17, which may be established via the Internet, a local area network, a wide area network, a telecommunications network or other appropriate communications network and may be a wireless communication link. A remote patient management system including central database 18 adapted for communication with monitor/programmer 16 may be embodied according to remote patient management systems known in the art. Examples of such systems are generally disclosed in U.S. Pat. No. 6,599,250 issued to Webb et al., U.S. Pat. No. 6,442,433 issued to Linberg, and U.S. Pat. No. 6,574,511 issued to Lee, U.S. Pat. No. 6,480,745 issued to Nelson et al., U.S. Pat. No. 6,418,346 issued to Nelson et al., and U.S. Pat. No. 6,250,309 issued to Krichen et al.

Figure 2:
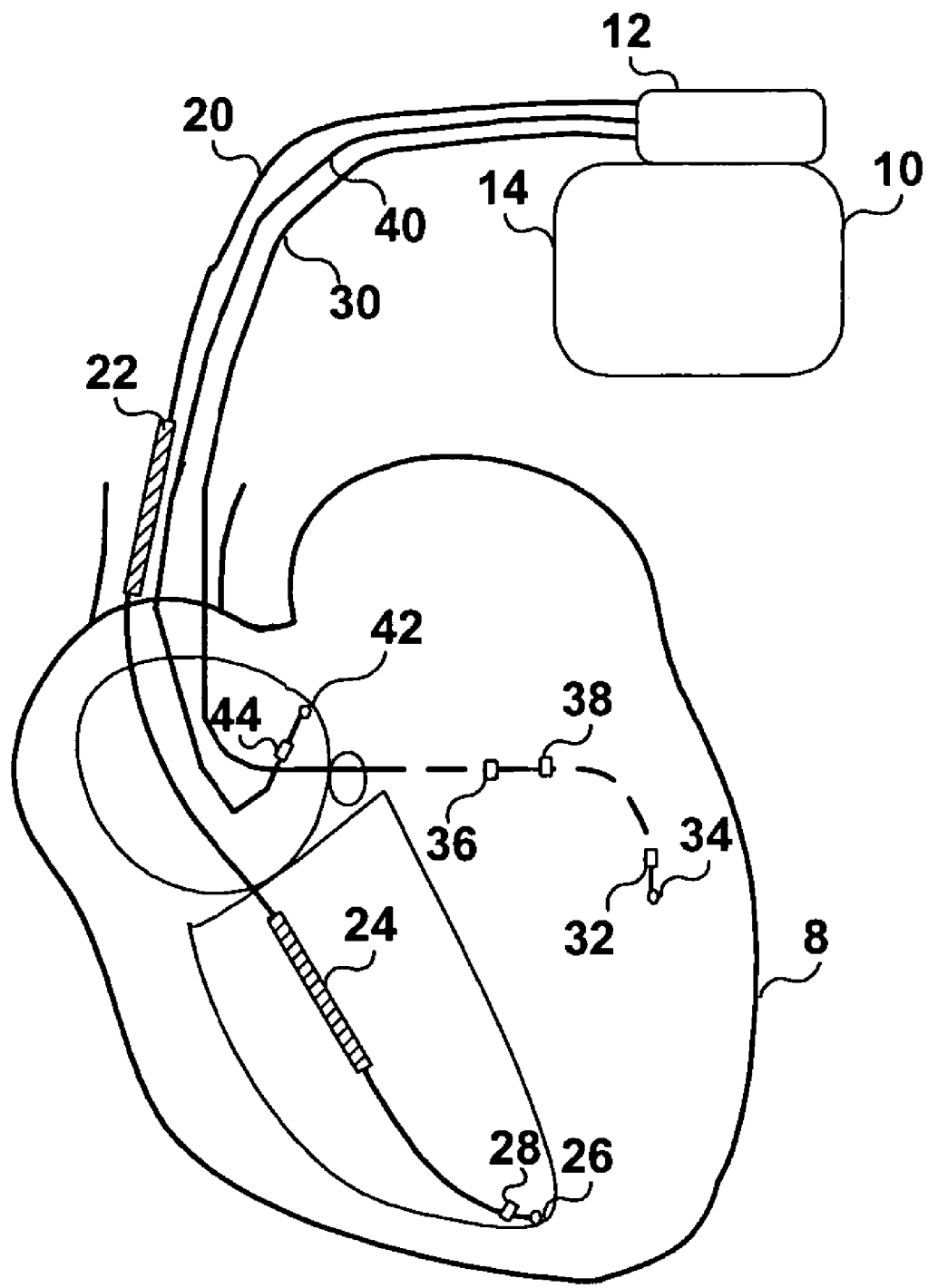
FIG. 2 illustrates one configuration of an IMD and associated cardiac leads in which various embodiments of the invention may be practiced.

FIG. 2 illustrates one configuration of IMD 10 and associated cardiac leads in which various embodiments of the invention may be practiced. IMD 10 is provided with a hermetically-sealed housing 14 enclosing control circuitry, such as a processor and associated memory, and other components as appropriate to produce the desired functionalities of IMD 10. IMD 10 includes a connector header 12 for receiving leads 20, 30 and 40 and facilitating electrical connection of leads 20, 30 and 40 to the components enclosed in housing 14.

IMD 10 is shown connected to a right ventricular (RV) cardiac lead 20, a coronary sinus (CS) lead 30 and a right atrial (RA) lead 40, although the particular cardiac leads used may vary from embodiment to embodiment. Each lead 20, 30 and 40 is deployed in operative relation to a patient's heart 8 for monitoring cardiac electrical signals and for delivering a stimulation therapy. RV lead 10 is provided with a tip electrode 26 and a ring electrode 28 which may be used as a bipolar sensing and/or pacing pair or individually in combination with IMD housing 14, also referred to herein as a "can" or "case" electrode, for unipolar sensing and/or pacing. If IMD 10 includes cardioversion and defibrillation functions, RV lead 20 may further include an RV coil electrode 24 and a superior vena cava (SVC) coil electrode 22 used together or in combination with IMD housing 10 in delivering high voltage cardioversion or defibrillation shocks.

CS lead 30 is provided with a tip electrode 34 and a ring electrode 32 used for sensing and pacing in the left ventricle (LV). CS lead 30 may also be provided with additional electrodes 36 and 38 positioned along CS lead 30 for use in sensing and pacing in the left atrium (LA). RA lead 40 is provided with tip electrode 42 and ring electrode 44 to acheive sensing and pacing in the right atrium. As shown, IMD 10 may be used for pacing and sensing in two, three, or all four heart chambers. It is recognized that in various embodiments of the invention, an IMD system may be configured for single, dual chamber or multi-chamber operation modes. Generally, in order to obtain ECG signals from both atrial and ventricular chambers, a lead system that includes electrodes that can be used for sensing far-field ventricular signals and electrodes for sensing far-field atrial signals is needed. The combination of ECG signals from different heart chambers may not be available using single chamber systems with a standard single chamber lead though ECG signals from a single chamber could be obtained. IMDs used for delivering a therapy to a single heart chamber, however, may be adapted for sensing ECG signals in more than one heart chamber with the use of alternative lead systems.

In operation, IMD 10 obtains data about heart 8 via leads 20, 30 and 40 and/or other sources. This data is provided to a processor enclosed in housing 14, which suitably analyzes the data, stores appropriate data in associated memory, and/or provides a response as appropriate. IMD 10 selects or adjusts a therapy and regulates the delivery of the therapy. In particular, IMD 10 regulates the delivery of cardiac stimulation pulses in one or more heart chambers based on analysis of EGM signals and timing intervals applied relative to EGM sensed events. In other embodiments, IMD 10 may deliver a drug, neural stimulation, or other therapy. IMD 10 may alternatively be embodied as a monitoring device used for collecting and storing EGM data, ECG data, and/or other physiological data for later retrieval and analysis using external monitor/programmer.

In accordance with one embodiment of the invention, ECG signals are obtained for use in patient follow-up sessions using selected far-field sensing electrodes on any of the available leads 20, 30 and 40. The ECG data so obtained is useful in evaluating the operation and performance of IMD 10. ECG signals are either collected and stored by IMD 10 for later transmission to the external monitor/programmer or transferred to the external/monitor programmer in real time. ECG signals so obtained may be used at the time of IMD implantation as well as at subsequent follow-up sessions.

Figure 3:
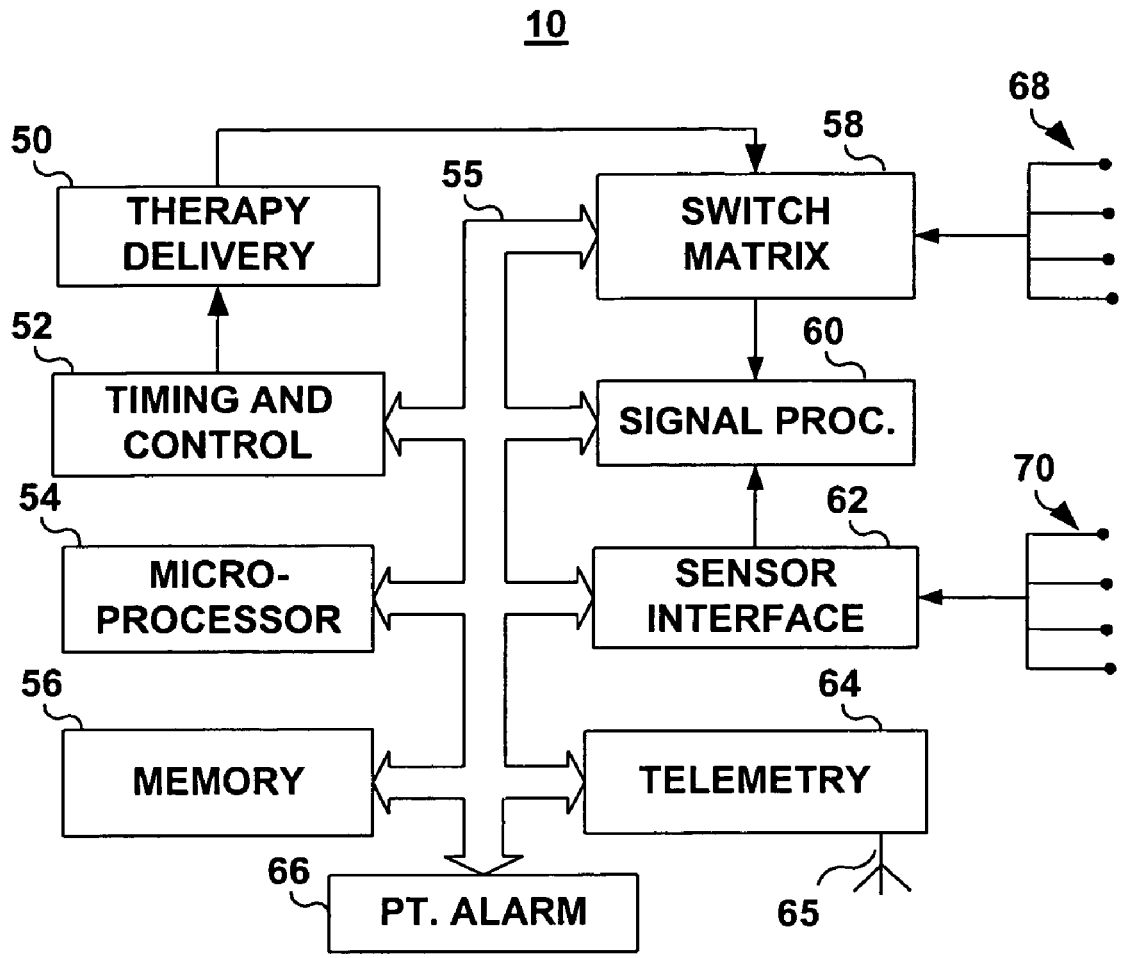
FIG. 3 is a block diagram of typical functional components of an IMD.

FIG. 3 is a block diagram of typical functional components of an IMD, such as IMD 10 shown in FIG. 2. IMD 10 generally includes timing and control circuitry 52 and an operating system that may employ microprocessor 54 or other operating system architecture such as a digital state machine for timing sensing and therapy delivery functions in accordance with a programmed operating mode. Microprocessor 54 and associated memory 56 are coupled to the various components of IMD 10 via a data/address bus 55. IMD 10 includes therapy delivery unit 50 for delivering a therapy, such as an electrical stimulation or drug therapy, under the control of timing and control 52. In the case of electrical stimulation therapies, such as cardiac stimulation therapies, therapy delivery unit 50 is typically coupled to two or more electrodes 68 via a switch matrix 58. With regard to the embodiment shown in FIG. 2, electrodes 68 collectively represent the electrodes 22, 24, 26, 28, 32, 34, 36, 38, 42, 44 and housing or "can" electrode 14. Switch matrix 58 is used for selecting which of the available electrodes are used for delivering stimulation pulses and their corresponding polarities.

Electrodes 68 are also used for sensing electrical signals within the body, including cardiac electrical signals, and may be used for measuring impedance. EGM signals are sensed for determining when a therapy is needed and in controlling the timing of therapy delivery relative to cardiac events. As will be described in greater detail herein, electrodes 68 are also selected for sensing ECG signals that are transferred to an external monitor and displayed or recorded for use in evaluating IMD 10 performance and operation and observing the patient's heart rhythm.

Electrodes used for sensing and electrodes used for stimulation may be selected via switch matrix 58. When used for sensing, electrodes 68 are coupled to signal processing circuitry 60, via switch matrix 58. Signal processor 60 includes sense amplifiers and may include other signal conditioning circuitry and an analog-to-digital converter. Cardiac electrical signals may then be used by microprocessor 54 for detecting physiological events, such as detecting and discriminating cardiac arrhythmias. In other embodiments, electrodes 68 may be used for measuring impedance signals for monitoring edema, respiration or heart chamber volume.

IMD 10 may additionally or alternatively be coupled to one or more physiological sensors 70. Such sensors may include pressure sensors, accelerometers, flow sensors, blood chemistry sensors, activity sensors or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, or patient activity. Monitored signals may be used for sensing the need for delivering a therapy under control of the operating system.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction from an external monitor/programmer. All of these functions and operations are known in the art, and generally employed to store operating commands and data for controlling device operation and for later retrieval to diagnose device function or patient condition.

IMD 10 includes telemetry circuitry 64 and associated antenna 65. Programming commands or data are transmitted during uplink or downlink telemetry session established between IMD telemetry circuitry 64 and external telemetry circuitry included in the external monitor/programmer. In particular, telemetry circuitry 64 and antenna 65 are used in transmitting ECG signals sensed by IMD 10 to an external monitor/programmer for providing an ECG signal display, recording and/or analysis.

Telemetry circuitry 64 and antenna 65 may correspond to telemetry systems known in the art. Telemetry circuitry 64 may embodied as a long range telemetry system that allows data to be transferred automatically when it is available without intervention by the patient. Long-range telemetry systems are generally disclosed in U.S. Pat. No. 6,482,154 issued to Haubrich et al., incorporated herein by reference in its entirety. In other embodiments, telemetry circuitry may require manual intervention to initiate or enable telemetry communication between IMD 10 and an external monitor/programmer. For example, telemetry circuitry 64 may require the use of an external programming head containing an external antenna to be positioned over IMD 10 as generally disclosed in U.S. Pat. No. 5,354,319 issued to Wyborny et al. Telemetry circuitry 64 may require manual "waking up" to enable data transmission or may require the patient to be within a limited communication range from the external monitor.

IMD 10 may be equipped with patient alarm circuitry 66 for generating audible tones, a perceptible vibration, muscle stimulation or other sensory stimulation for notifying the patient that a patient alert condition has been detected by IMD 10. A patient alert condition may be defined with regard to any of the monitoring functions provided by IMD 10.

Figure 4:
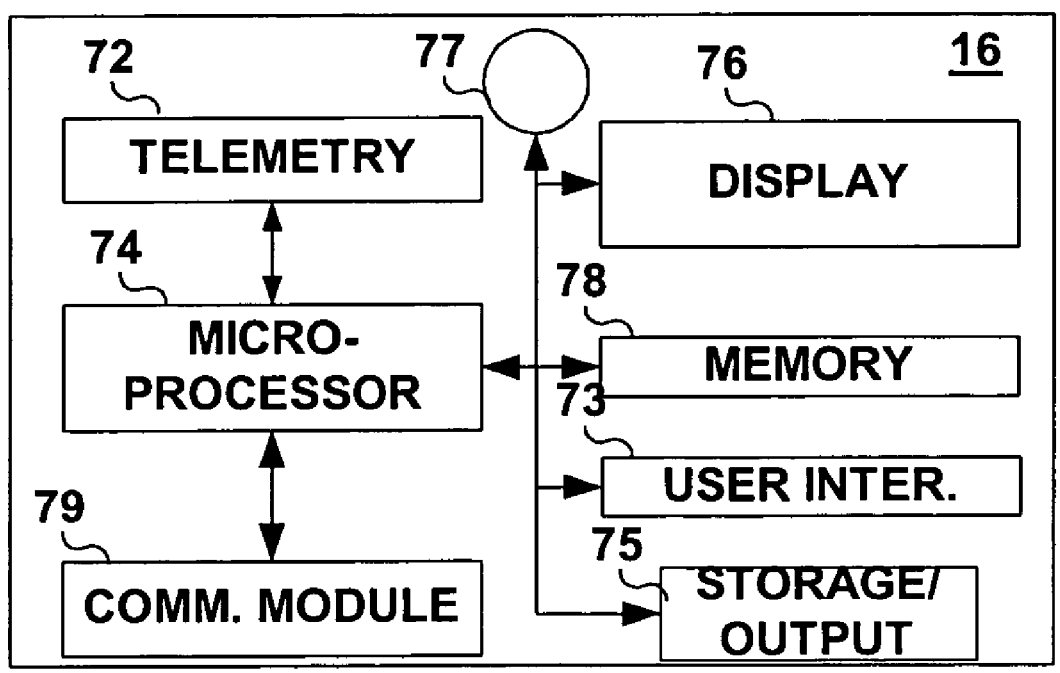
FIG. 4 is a functional block diagram of typical components included in an external monitor/programmer.

FIG. 4 is a functional block diagram of typical components included in an external monitor/programmer. External monitor/programmer 16 may be a microprocessor-controlled device wherein microprocessor 74 operates with associated memory 78 for controlling monitor/programmer functions. External monitor/programmer 16 includes a telemetry circuit 72 for communicating with IMD 10. External monitor/programmer 16 is used for retrieving data from IMD 10. Retrieved data may be displayed on display 76, stored in memory 78 or provided to storage/output interface 75. Storage/output interface 75 may write data to an electronic data storage medium, such as a DVD or CD ROM drive, or provide data to a printer or other recording device. In particular, external monitor/programmer 16 receives ECG data from IMD 10 obtained using available implanted cardiac electrodes as will be described in greater detail below. ECG data can be displayed on display 76 and/or provided to storage/output interface 75 for storing or recording.

External monitor/programmer 16 may be used to downlink programming instructions and operating parameter values to be implemented by IMD 10 for controlling IMD functions. External monitor/programmer 16 may further include a speaker 77 for generating audible tones during telemetry sessions. In some embodiments, external monitor/programmer 16 includes a user interface 73 for entering commands or programming information if external monitor 20 is enabled to perform programming functions. User interface 73 may be used to enter data retrieval or transmission requests, manipulate display 76, enter printing and storage commands, or otherwise manually control external monitor/programmer operations.

External monitor/programmer 16 may include a communications module 79, to allow data transmission via a communication network. Communications module 79 may be embodied as a hardwired or wireless modem or other communication network interface. External monitor/programmer 16 may transmit data to a remote patient management database via the communication network as described previously. In particular, during a remote patient follow-up session, ECG data may be transferred from the IMD to external monitor/programmer 16 and on to a remote patient management database to allow a clinician to view ECG data obtained by the IMD in real-time or at a later time. A clinician can remotely evaluate IMD operation and performance using the ECG data and make programming changes or other recommendations as appropriate.

ECG data retrieved from an IMD may also undergo signal analysis operations performed according to algorithms executed by microprocessor 74 or by a processor included in a remote patient management system associated with the central database 18 shown in FIG. 1. ECG data may be analyzed for, but not limited to: determining incidence of capture or loss of capture, fusion pacing, changes in P-wave duration, changes in QRS duration, changes in P-R intervals, changes in S-T intervals, changes in S-T segment elevation, frequency of pacing, heart rate, predominate heart rhythm. Any analyses of ECG signals normally performed using single lead, surface ECG signals may be performed using the ECG signals obtained by the IMD and transferred to the external monitor/programmer 16.

Figure 5:
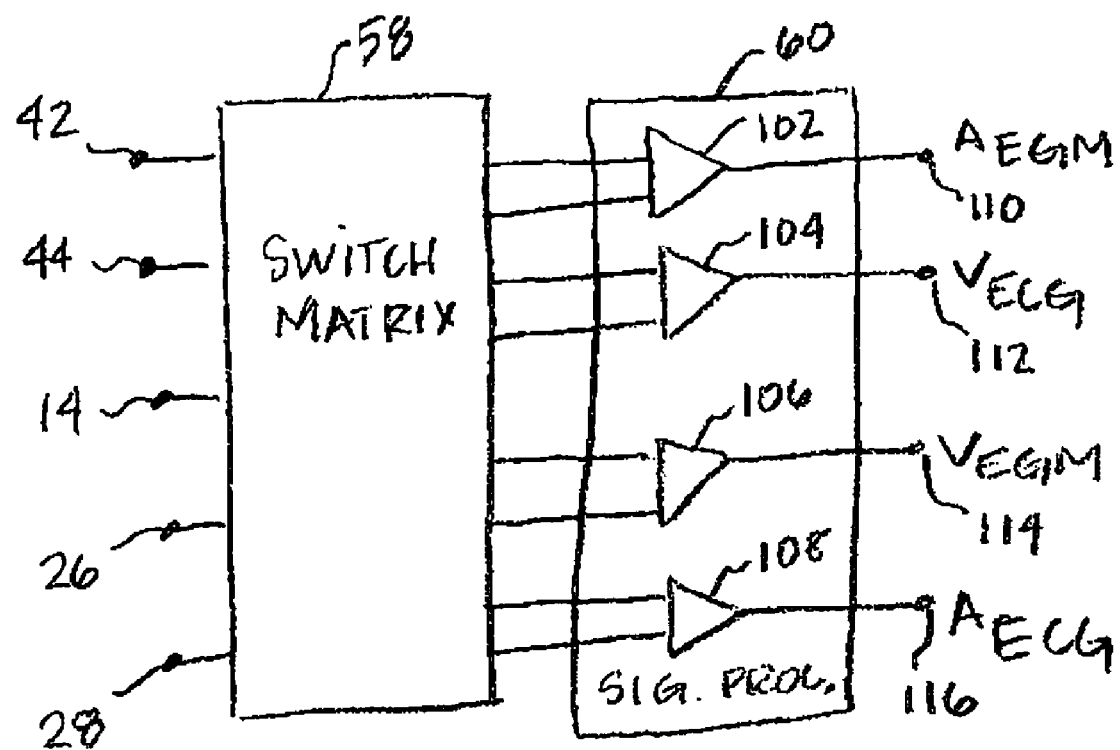
FIG. 5 is a block diagram illustrating cardiac sensing functions according to one embodiment of the invention.

FIG. 5 is a block diagram illustrating cardiac sensing functions according to one embodiment of the invention. ECG signals sensed using implanted, far-field cardiac electrodes provide information analogous to that obtained using surface ECG electrodes and are therefore useful in evaluating IMD performance and operation and the patient's heart rhythm. In order to obtain ECG signals using implanted electrodes, signals corresponding to electrical events occurring in a cardiac chamber are obtained using far-field sensing electrodes positioned outside of that cardiac chamber. For example, ECG signals corresponding to ventricular events may be obtained using atrial sensing electrodes, and ECG signals corresponding to atrial events may be obtained using ventricular sensing electrodes. One arrangement for sensing atrial and ventricular EGM and ECG signals is illustrated in FIG. 5.

RA tip electrode 42, RA ring electrode 44, "can" electrode 14, RV tip electrode 26 and RV ring electrode 28 are shown coupled to switch matrix 58. Switch matrix 58 is used to select which electrodes are coupled to various sense amplifiers included in signal processing circuitry 60. An atrial EGM sense amplifier 102 receives a selected atrial sensing electrode pair, for example RA tip electrode 42 and RA ring electrode 44 or either of RA tip electrode 42 and RA ring electrode 44 with "can" electrode 14 for sensing atrial EGM signals. The signal sensed using atrial sensing electrodes includes far-field ventricular signals, similar to that obtained using surface ECG electrodes. During normal IMD operation, atrial sensing electrodes are coupled to atrial EGM sense amplifier 102 to allow the IMD to sense the occurrence of intrinsic or evoked atrial P-waves for use in detecting the cardiac rhythm and in regulating the delivery of cardiac stimulation pulses. The gain of atrial EGM sense amplifier 102 is adjusted to provide a signal-to-noise ratio that allows atrial events to be reliably sensed without oversensing of ventricular events or other non-atrial electrical events. Blanking intervals may be applied to atrial EGM sense amplifier 102 during the delivery of pacing pulses as known in the art. Atrial EGM sense amplifier 102 may be enabled for sensing atrial signals during a defined time interval corresponding to P-wave occurrence. The atrial EGM output (A EGM) 110 is provided to timing and control circuitry 52 and/or processor 54 (shown in FIG. 3) for use in detecting the cardiac rhythm and controlling therapy delivery. Acquisition of an atrial EGM signal 110 may be performed using sense amplifiers and according to methods known in the art.

In order to obtain a ventricular ECG signal (V ECG) 112, atrial sensing electrodes are coupled to a ventricular ECG sense amplifier 104 via switch matrix 58. The same or different atrial sensing electrode pairs may be coupled to ventricular ECG sense amplifier 104 and atrial EGM sense amplifier 102. A ventricular ECG sensing window is applied to ventricular ECG sense amplifier 104 to enable the sense amplifier 104 for sensing during a time interval corresponding to ventricular electrical events, for example the QRS complex and the T-wave. The gain of ventricular ECG sense amplifier 104 is adjusted to provide an acceptable ventricular signal-to-noise ratio. By enabling the ventricular ECG sense amplifier during a ventricular ECG sensing window, the near-field atrial signals, that would normally be greater in magnitude than the far-field ventricular signals, are not sensed. The amplitude resolution of the sensed signals can thereby be adjusted to observe ventricular events for use in ECG analyses performed during IMD follow-up evaluations.

The atrial EGM sense amplifier 102 and ventricular ECG sense amplifier 104 are shown as distinctly separate sense amplifiers in FIG. 5. Both sense amplifiers may be operating simultaneously for acquiring atrial EGM signals and ventricular ECG signals at separately selected gains appropriate for each function. In some embodiments, a single sense amplifier may be provided having an adjustable gain that allows atrial EGM signals to be acquired during an atrial EGM sensing window at one gain setting and ventricular ECG signals to be acquired during a ventricular ECG sensing window at a different gain setting.

A ventricular EGM sense amplifier 106 is coupled to a selected ventricular sensing electrode pair via switch matrix 58. For example RV tip electrode 26 and RV ring electrode 28, or either of RV tip electrode 26 and RV ring electrode 28 with "can" electrode 14, may be used for sensing ventricular EGM signals. The signal sensed using ventricular sensing electrodes will include far-field atrial signals, similar to atrial signals obtained using surface ECG electrodes. During normal IMD operation, ventricular sensing electrodes are coupled to ventricular EGM sense amplifier 106 to allow the IMD to sense the occurrence of intrinsic or evoked R-waves for use in detecting the cardiac rhythm and in regulating the delivery of cardiac stimulation pulses. The gain of ventricular EGM sense amplifier 106 is adjusted to provide a signal-to-noise ratio that allows R-waves to be reliably sensed without oversensing of atrial events or other non-ventricular electrical events. Blanking intervals may be applied to ventricular sense amplifier 106 during the delivery of pacing pulses as known in the art. Ventricular EGM sense amplifier 106 may be enabled for sensing atrial signals during a defined time interval corresponding to R-wave occurrence. The ventricular EGM output (V EGM) 114 is provided to timing and control circuitry 52 and/or processor 54 (shown in FIG. 3) for use in detecting the cardiac rhythm and controlling therapy delivery.

In order to obtain an atrial ECG signal (A ECG) 116, ventricular sensing electrodes are coupled to an atrial ECG sense amplifier 108 via switch matrix 58. The same or different ventricular sensing electrode pairs may be coupled to ventricular EGM sense amplifier 106 and atrial ECG sense amplifier 108. An atrial ECG sensing window is applied to atrial ECG sense amplifier 108 to enable the sense amplifier 108 during a time interval corresponding to atrial P-waves. The gain of atrial ECG sense amplifier 108 is adjusted to provide an acceptable atrial signal-to-noise ratio. By enabling the atrial ECG sense amplifier during an atrial ECG sensing window, the near-field ventricular signals, that would normally be greater in magnitude than the far-field atrial signals, are not sensed. The amplitude resolution of the sensed signals can thereby be adjusted to adequately observe atrial events for use in ECG analyses performed during IMD follow-up evaluations.

The ventricular EGM sense amplifier 106 and atrial ECG sense amplifier 116 are shown as distinctly separate sense amplifiers in FIG. 5. Both sense amplifiers may be operating simultaneously for acquiring atrial ECG signals and ventricular EGM signals at separately selected gains, appropriate for each function. In some embodiments, a single sense amplifier may be provided having an adjustable gain that allows ventricular EGM signals to be acquired during a ventricular EGM sensing window at one gain setting and atrial ECG signals to be acquired during an atrial ECG sensing window at a different gain setting. The various sense amplifiers described herein may correspond to automatic gain control sense amplifiers. The use of automatic gain control sense amplifiers is known in the art, for example as generally described in U.S. Pat. No. 5,117,824 by Keimel et al.

The atrial ECG signal 116 and the ventricular ECG signal 112 are stored in IMD memory 56 (shown in FIG. 3) or transmitted to an external monitor/programmer via IMD telemetry circuitry 64 (FIG. 3). Although the use of right atrial sensing electrodes and right ventricular sensing electrodes is illustrated in FIG. 5, it is recognized the, when available, left atrial and/or left ventricular sensing electrodes may alternatively or additionally be used in any combination for selecting far-field sensing electrode pairs for use in acquiring ECG signals.

Figure 6:
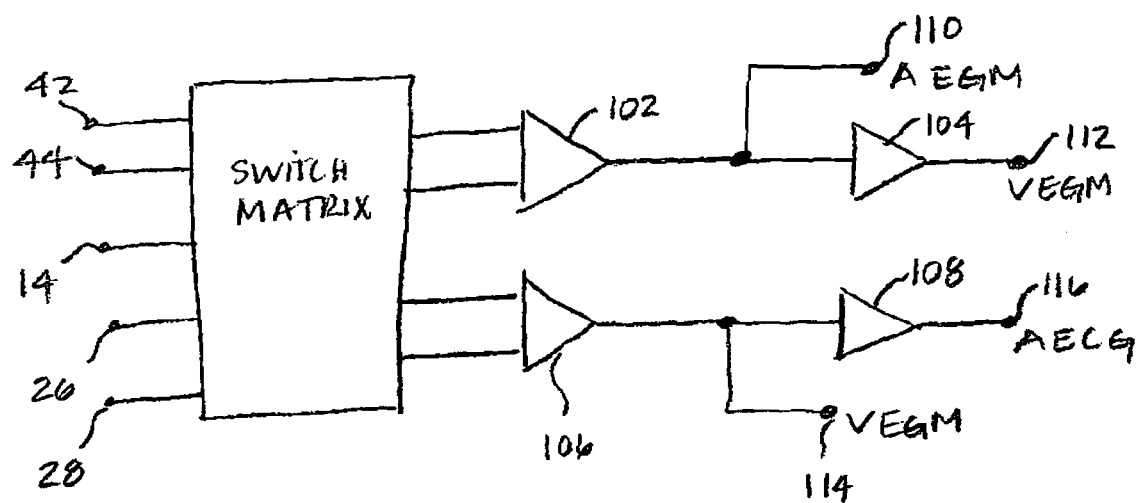
FIG. 6 is a block diagram illustrating an alternative embodiment for acquiring cardiac electrical signals by an IMD.

FIG. 6 is a functional block diagram illustrating an alternative embodiment for acquiring cardiac electrical signals by an IMD. Selected atrial sensing electrodes are coupled to atrial sense amplifier 102 having a gain setting for providing an atrial EGM signal 110. The atrial EGM signal 110 is acquired continuously (with blanking intervals applied as appropriate) and provided as input to a ventricular ECG sense amplifier 104. Ventricular ECG sense amplifier 104 is enabled during a sensing window corresponding to ventricular events (QRS complex and T-wave) with a gain setting appropriate for providing adequate resolution of ventricular ECG signal 112 for ECG signal analysis.

Likewise, selected ventricular sensing electrodes are provided as input to ventricular EGM sense amplifier 106, having a gain setting for providing a ventricular EGM signal 114. Ventricular EGM signal 114 is provided as input to atrial ECG sense amplifier 108, enabled during a sensing window corresponding to atrial events (P-waves) with a gain setting for providing adequate resolution of an atrial ECG signal 116 for ECG signal analysis.

Figure 7:
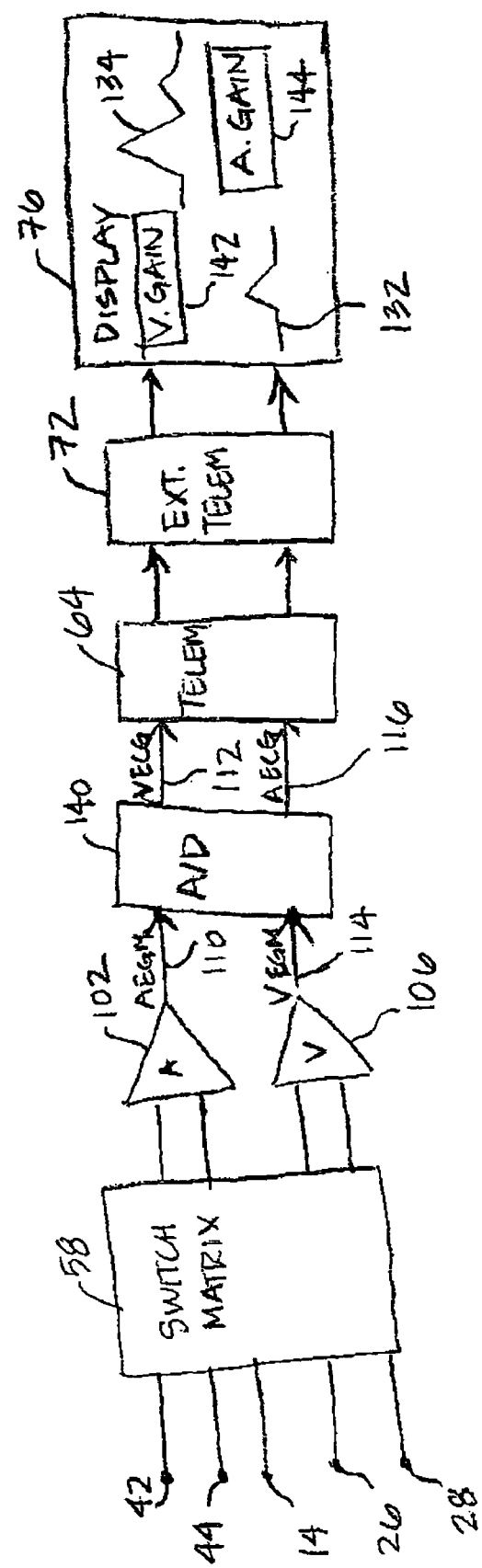
FIG. 7 is a functional block diagram illustrating yet another embodiment for acquiring ECG signals by an IMD.

FIG. 7 is a functional block diagram illustrating yet another embodiment for acquiring ECG signals by an IMD. Switch matrix 58 is used to select which electrodes 42, 44, 26, 28 and 14 are coupled to atrial EGM sense amplifier 102 and ventricular EGM sense amplifier 106. The output of atrial EGM sense amplifier 102, atrial EGM signal 110, and the output of ventricular EGM sense amplifier 106, ventricular EGM signal 114, are provided to an A/D converter 140, which may be included in signal processor 60 (FIG. 3) for digitizing the sensed signals. The atrial EGM signal 110 is digitized over ventricular ECG sensing window, and the ventricular EGM signal 114 is digitized over an atrial ECG sensing signal. The resulting ventricular ECG signal 112 and atrial ECG signal 116 are transferred via IMD telemetry circuit 64 to external monitor/programmer telemetry circuit 72.

A ventricular ECG signal display 134 and an atrial ECG signal display 144 are provided on display 76. A ventricular gain control 142 and an atrial gain control 144 are provided for separately adjusting the gain of each of the ventricular ECG signal display 134 and atrial ECG signal display 144, respectively. As such, the ECG signals may be acquired by the IMD using the conventional atrial and ventricular EGM sense amplifiers tuned to respective gains appropriate for acquiring atrial and ventricular EGM signals. The gain of the ventricular and atrial ECG signals acquired from the EGM signals during appropriate sensing windows can be adjusted by a user interacting with the external monitor/programmer for obtaining a desired resolution of the signals displayed.

Figure 8:
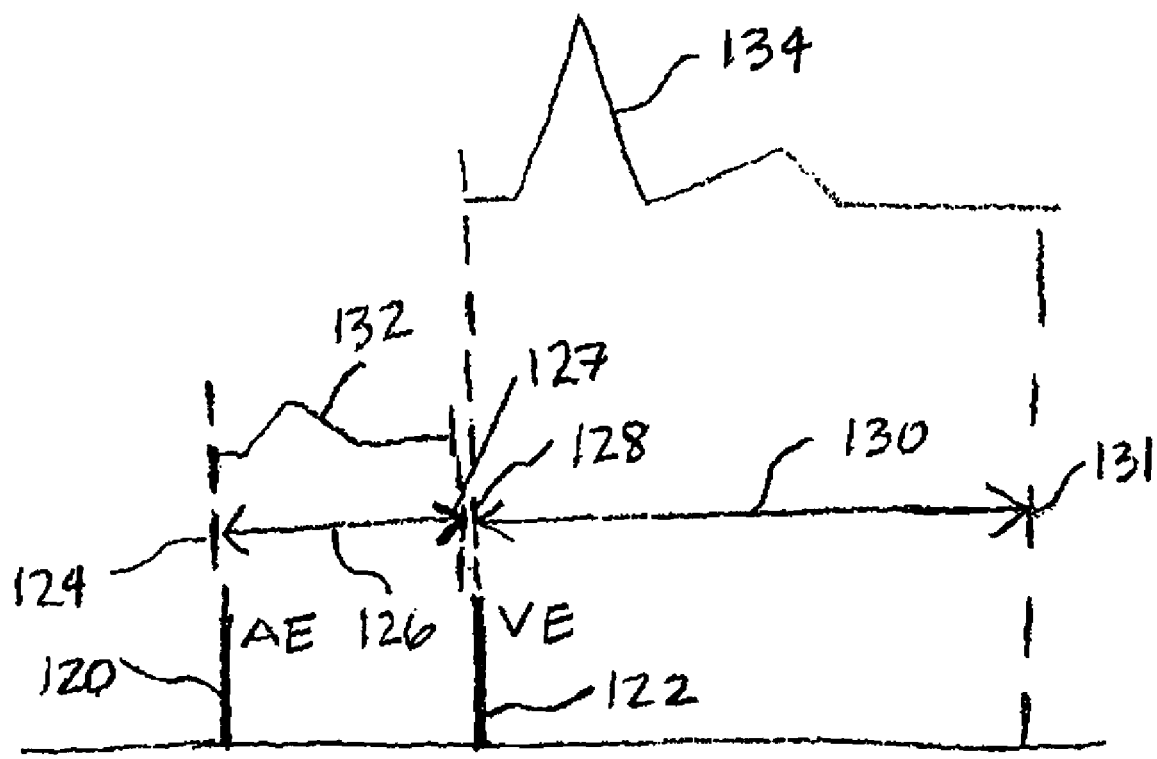
FIG. 8 is a timing diagram illustrating sensing windows that may be used for obtaining ECG signals using implanted cardiac electrodes.

FIG. 8 is a timing diagram illustrating sensing windows that may be used for obtaining ECG signals using implanted cardiac electrodes. An atrial ECG sensing window 126 and a ventricular ECG sensing window 130 are set relative to sensed or paced cardiac events 120 and/or 122. The atrial ECG sensing window 126 may be defined relative to an atrial event 120 for enabling a sense amplifier coupled to ventricular sensing electrodes. For example, a starting point 1124 for atrial ECG sensing window 126 may be set relative to atrial event 126, which may be an atrial pacing pulse delivered by the IMD or a P-wave sensed using a sensed EGM signal. The starting point 124 for atrial ECG sensing window 126 may be defined after an atrial pacing pulse to avoid saturation of the sense amplifier by the atrial pacing pulse. The duration of atrial ECG sensing window 126 may be a fixed duration following atrial event 120. Alternatively, the atrial ECG sensing window duration may be variable with an end point 127 corresponding to the occurrence of a sensed or paced ventricular event 122. Atrial ECG signal 132 is acquired during atrial ECG sensing window 126.

A ventricular ECG sensing window 130 is used to enable a sense amplifier coupled to atrial sensing electrodes. The ventricular ECG sensing window 130 may be set relative to a ventricular event 122. For example, a starting point 128 for a ventricular ECG sensing window 130 may be set relative to a ventricular pacing pulse delivered by the IMD or an R-wave sensed from an EGM signal. The starting point 128 for ventricular ECG sensing window 130 may be defined after a ventricular pacing pulse to avoid saturation of the sense amplifier by the pacing pulse. The duration of ventricular ECG sensing window may be a fixed duration following a ventricular event 122. Alternatively, the ventricular ECG sensing window duration may be variable with an end point corresponding to the occurrence of a subsequent atrial event. Ventricular ECG signal 134 is acquired using atrial sensing electrodes coupled to a sense amplifier enabled during ventricular ECG sensing window 130.

In some embodiments, atrial ECG sensing window 126 and ventricular ECG sensing window may be defined relative to one paced or sensed event. For example, ventricular ECG sensing window 130 may be defined relative to ventricular event 122 and set for an set for a pre-defined duration, for example 400 ms. The atrial ECG sensing window 126 may be defined relative to the ventricular ECG sensing window 130, for example relative to the end point 131 of ventricular ECG sensing window 130, and set of a pre-defined duration, for example 200 ms. A portion of the ventricular ECG sensing window 130 and the subsequent atrial ECG sensing window 132 may overlap to allow for variations in heart rate. It is appreciated that the timing definitions of atrial ECG sensing window 126 and ventricular ECG sensing window 130 may vary between embodiments.

Atrial ECG signal 132 and ventricular ECG signal 134 may be displayed by external monitor/programmer 16 (FIG. 1) in separate windows or merged and displayed in a single window. Atrial ECG signal 132 and ventricular ECG signal 134 may be displayed with marker channel data or other data provided by IMD 10 for facilitating evaluation of IMD operation. For example, atrial ECG signal 132 and ventricular ECG signal 134 may be used for verifying capture of pacing pulses. If loss of capture or fusion is observed, adjustments may be made to the pacing pulse energy, pacing intervals, or other pacing control parameters as appropriate.

Atrial ECG signal 132 and ventricular ECG signal 134 may also be used in performing other analyses that normally require acquisition of surface ECG signals. For example, observations may be made regarding the frequency of pacing, ECG changes associated with ischemia, the duration of P-waves and R-waves, or the like.

Figure 9:
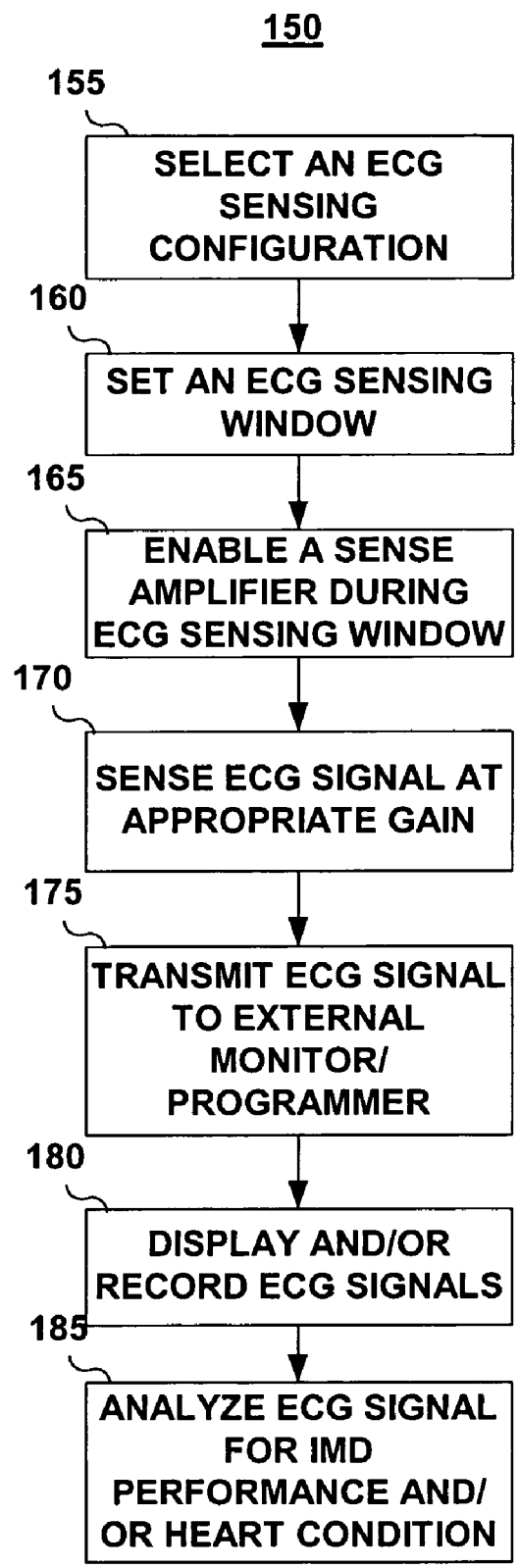
FIG. 9 is a flow chart summarizing steps included in a method for obtaining ECG signals using implanted electrodes.

FIG. 9 is a flow chart summarizing steps included in a method for obtaining ECG signals using implanted electrodes. At step 155 of method 150, an ECG sensing electrode configuration is selected for sensing ECG signals originating from one or more heart chambers and coupled to appropriate sense amplifier(s). As described previously, a far-field electrode pair is selected for sensing signals occurring in a cardiac chamber. An atrial sensing electrode pair normally available for sensing atrial EGM signals may be selected for sensing ventricular ECG signals, and a ventricular sensing electrode pair normally available for sensing ventricular EGM signals may be selected for sensing atrial ECG signals.

At step 160 ECG sensing window(s) are set relative to paced or intrinsic cardiac events for appropriately sensing ECG signals in a cardiac chamber using the selected far-field sensing electrodes. Various approaches for setting ECG sensing windows may be used as described in conjunction with FIG. 8. At step 165, the sense amplifier(s) used for sensing the ECG signal(s) are enabled during the ECG sensing window (s).

At step 170, the ECG signal(s) are sensed during the sensing window(s) using the selected far-field electrode pair(s). The sense amplifier(s) are set to appropriate gain levels to provide adequate resolution of the far-field ECG signals obtained during the sensing window(s). In alternative embodiments, ECG signals may be acquired continuously and digitized over a desired sensing window. Gain adjustments may additionally or alternatively be made using the external monitor/programmer after signal transmission to the external monitor/programmer.

At step 175, the ECG signals are transmitted to an external monitor/programmer. The ECG signals are displayed and/or stored or recorded at step 180. The ECG signals may be transmitted in real time at step 175 or stored for a period of time by the IMD prior to transmission.

At step 185, automated analysis of the transmitted ECG signals may be performed. Transmitted ECG signals may be provided to a processor included in external monitor/programmer or another computer for performing automated ECG signal analysis. Automated analyses of transmitted ECG signals may include evaluations of IMD performance, such as, but not limited to, determining: capture or loss of capture, fusion, and frequency of pacing or other delivered therapies. Automated analyses of transmitted ECG signals may additionally or alternatively be performed to evaluate a heart condition. Heart conditions that may be determined using the transmitted ECG signals may include, but are not limited to: predominate heart rhythm, presence of arrhythmias, ectopy, and ischemia.

Thus, methods and apparatus for acquiring ECG signals without the use of surface ECG electrodes has been presented in the foregoing description with reference to specific embodiments. It is appreciated that. various modifications to the referenced embodiments may be made without departing from the scope of the invention as set forth in the following claims.

The invention claimed is:

1. A method comprising:
   selecting a first sensing electrode configuration that includes at least one electrode operatively disposed along a first heart chamber;
   selecting a second sensing electrode configuration that includes at least one electrode operatively disposed along a second heart chamber;
   setting a first sensing window corresponding to cardiac electrical events occurring in the second heart chamber;
   setting a second sensing window corresponding to cardiac electrical events occurring in the first heart chamber;
   enabling a first sense amplifier coupled to the first sensing electrode configuration;
   enabling a second sense amplifier coupled to the second sensing electrode configuration;
   sensing a first signal corresponding to cardiac electrical events occurring in the second heart chamber during the first sensing window using the first sensing electrode configuration, wherein a signal-to-noise ratio of the first sense amplifier is adjusted to preclude sensing of the second signal and a signal-to-noise ratio of the second sense amplifier is adjusted to preclude sensing of the first signal;
   sensing a second signal corresponding to cardiac electrical events occurring in the first heart chamber during the second sensing window using the second sensing electrode configuration;
   transmitting the first signal and the second signal from an implantable medical device to an external monitor during a telemetry session;
   receiving, with the external monitor, the first signal and the second signal from the implantable medical device during the telemetry session;
   separately adjusting, at the external monitor, a gain of each of the respective first signal and the second signal received from the implantable medical device;
   merging the adjusted first signal and the second signal into a single merged signal; and
   displaying the single merged signal on a display of the external monitor to provide an ECG signal.

2. The method of claim 1 further including delivering a first pacing pulse to the second heart chamber and wherein setting the first sensing window includes setting a starting time corresponding to the first pacing pulse.

3. The method of claim 1 further including delivering a first pacing pulse to the second heart chamber and verifying capture of the second heart chamber using the transmitted signals.

4. The method of claim 1 further including delivering a second pacing pulse to the first heart chamber and wherein setting the second sensing window includes setting a second starting time corresponding to the second pacing pulse.

5. The method of claim 1 further including delivering a second pacing pulse to the first heart chamber and verifying capture of the first heart chamber using the transmitted signals.

6. The method of claim 1, further including evaluating the performance of the implantable medical device using the transmitted signals.

7. The method of claim 1, further including determining a heart condition using the transmitted signals.

8. The method of claim 1 further comprising receiving a command from an external device to transmit the first and second signals to the external monitor in real time.

9. The method of claim 1 wherein setting the second window comprises setting the second window relative to the end point of the first window.

10. The method of claim 9 wherein the first window and the second window are set to overlap.

11. The method of claim 1, further comprising:
   sensing a third signal corresponding to cardiac electrical events occurring in the first heart chamber during the second sensing window using the first sensing electrode configuration;
   amplifying the first signal and the third signal using the first sense amplifier;
   sensing a fourth signal corresponding to cardiac electrical events occurring in the second heart chamber during the first sensing window using the second sensing electrode configuration; and
   amplifying the second signal and the fourth signal using the second sense amplifier.

12. The method of claim 1, wherein displaying the single merged signal on the display of the external monitor comprises merging the first signal and second signal based on the first and second timing windows to obtain the ECG signal.

13. The method of claim 1, wherein sensing the first signal comprises sensing a first electrocardiogram (ECG) signal corresponding to cardiac electrical events occurring in the second heart chamber during the first sensing window using the first sensing electrode configuration;
sensing the second signal comprises sensing a second electrocardiogram (ECG) signal corresponding to cardiac electrical events occurring in the first heart chamber during the second sensing window using the second sensing electrode configuration; and
displaying the first and second signal comprises displaying the first and second ECG signal on the display of the external monitor.

14. A medical system, comprising:
a telemetry circuit to communicate with an implantable medical device, wherein the telemetry circuit receives a first signal from the implantable medical device corresponding to cardiac electrical events occurring in a second heart chamber sensed during a first sensing window using a first electrode configuration that includes at least one electrode operatively disposed along a first heart chamber and receives a second signal from the implantable medical device corresponding to cardiac electrical events occurring in the first heart chamber sensed during a second sensing window using a second electrode configuration that includes at least one electrode operatively disposed along the second heart chamber, wherein the implantable medical device includes a first sense amplifier having a signal-to-noise ratio that precludes sensing of the second signal and a second sense amplifier having a signal-to-noise ratio that precludes sensing of the first signal;
a user interface having at least one gain control to separately adjust a gain of each of the respective first signal and the second signal received from the implantable medical device; and
a processor to acquire an ECG signal, wherein the acquired ECG signal is created by merging the first signal and the second signal; and
a display to display the acquired ECG signal.

15. The medical system of claim 14, wherein the processor merges the first signal and the second signal to obtain the ECG signal similar to a surface ECG signal.

16. The medical system of claim 15, wherein the processor merges the first signal and second signal based on the first and second timing windows to obtain the ECG signal similar to a surface ECG signal.

17. A method comprising:
receiving, with an external monitor, a first signal from an implantable medical device corresponding to cardiac electrical events occurring in a second heart chamber sensed during a first sensing window using a first electrode configuration that includes at least one electrode operatively disposed along a first heart chamber;
receiving, with the external monitor, a second signal from the implantable medical device corresponding to cardiac electrical events occurring in the first heart chamber sensed during a second sensing window using a second electrode configuration that includes at least one electrode operatively disposed along the second heart chamber, wherein the implantable medical device includes a first sense amplifier having a signal-to-noise ratio that precludes sensing of the second signal and a second sense amplifier having a signal-to-noise ratio that precludes sensing of the first signal;
merging the first signal and the second signal into a single merged signal; and
displaying the single merged signal on a display of the external monitor to provide an ECG signal.

* * * * *